United States Patent [19]
Boney et al.

[11] Patent Number: 5,932,495
[45] Date of Patent: Aug. 3, 1999

[54] ENHANCED ODOR ABSORPTION BY NATURAL AND SYNTHETIC POLYMERS

[75] Inventors: Lee Cullen Boney, Roswell; Richard Arnold Borders, Marietta; Robert Cosmo Di Luccio, Alpharetta, all of Ga.; Eric Scott Kepner, Fletcher, N.C.; Ali Yahiaoui, Roswell, Ga.

[73] Assignee: Kimberly-Clark Worldwide, Inc., Neenah, Wis.

[21] Appl. No.: 09/087,686

[22] Filed: May 29, 1998

Related U.S. Application Data

[63] Continuation-in-part of application No. 08/994,828, Dec. 19, 1997, which is a continuation-in-part of application No. 08/898,188
[60] Provisional application No. 60/025,621, Sep. 4, 1996.
[51] Int. Cl.⁶ ........................................ A61F 13/00
[52] U.S. Cl. .................... 442/121; 442/123; 442/164; 428/532; 604/359
[58] Field of Search ................... 428/532; 442/121, 442/123, 164; 604/359

[56] References Cited

U.S. PATENT DOCUMENTS

| | | | |
|---|---|---|---|
| 3,338,992 | 8/1967 | Kinney | 264/24 |
| 3,341,394 | 9/1967 | Kinney | 161/72 |
| 3,502,538 | 3/1970 | Petersen | 161/150 |
| 3,502,763 | 3/1970 | Hartmann | 264/210 |
| 3,542,615 | 11/1970 | Dobo et al. | 156/181 |
| 3,692,618 | 9/1972 | Dorschner et al. | 161/72 |
| 3,802,817 | 4/1974 | Matsuki et al. | 425/66 |
| 3,855,046 | 12/1974 | Hansen et al. | 161/150 |
| 4,340,563 | 7/1982 | Appel et al. | 264/518 |
| 4,846,823 | 7/1989 | Enloe | 604/385.2 |
| 4,846,825 | 7/1989 | Enloe et al. | 604/385.1 |
| 4,990,339 | 2/1991 | Scholl et al. | 424/443 |
| 5,108,820 | 4/1992 | Kaneko et al. | 428/198 |
| 5,108,827 | 4/1992 | Gessner | 428/219 |
| 5,336,552 | 8/1994 | Strack et al. | 428/224 |
| 5,382,400 | 1/1995 | Pike et al. | 264/168 |
| 5,763,067 | 6/1998 | Bruggemann et al. | 428/317.9 |
| 5,795,916 | 8/1998 | Sekine et al. | 514/567 |

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

*Primary Examiner*—Jenna Davis
*Attorney, Agent, or Firm*—William D. Herrick

[57] ABSTRACT

Odor reduction for products such as disposable diapers and training pants, sanitary napkins and tampons, incontinent products, and medical dressings is obtained by the use of an internal additive for synthetic polymers or an external additive for natural polymers. Results are further enhanced by the use of a surfactant especially in the case of synthetic polymers. Webs, fibers and films find uses as components of the described products and are effective in absorbing odors such as ammonia, triethylamine, indole and skatole, for example, which are commonly found in body fluids like sweat, menses, urine and fecal matter.

15 Claims, No Drawings

ENHANCED ODOR ABSORPTION BY NATURAL AND SYNTHETIC POLYMERS

This application is a continuation-in-part of application Ser. No. 08/994,828 entitled "Method and Composition for Treating Substrates for Wettability" and filed in the U.S. Patent and Trademark Office on Dec. 19, 1997, pending, which is a continuation-in-part of application Ser. No. 08/898,188 entitled "Method and Composition for Treating Substrates for Wettability", pending, and claims priority from U.S. Provisional Application Ser. No. 60/025,621 entitled "Method and composition for Treating Substrates for Wettability" filed on Sep. 4, 1996. The entirety of each of these referenced applications is hereby incorporated by reference.

BACKGROUND OF THE INVENTION

1. Field of the Invention

The present invention is directed to devices, compositions and structures that are exposed to odoriferous conditions and enhancement of the ability of such compositions and structures to absorb malodors. Examples include nonwoven webs or components of products such as disposable diapers, sanitary napkins, incontinent products, underarm pads and the like that are used to absorb sweat, urine, feces or other bodily exudates.

2. Background

Considerable success has been achieved in the design of products intended to absorb and retain human and animal waste materials. The construction of articles such as disposable diapers and training pants, sanitary napkins and tampons, incontinent products and hospital dressings, for example has become sophisticated with the addition of elastics, barrier cuffs, and the like to retain the waste and prevent leakage. Reference may be had to US Pat. Nos. 4,846,823 to Enloe and 4,846,825 to Enloe et al. for examples of these products as disposable diapers. The control of odor, on the other hand, remains a challenge that is exacerbated by the design success mentioned above which has led to larger quantities of waste being contained in products designed to require changing less frequently. Moreover, the desire for breathability in such products for increased comfort has added to the odor control challenge.

Most odors from body fluids contain bacterial derived components and degradation products associated with biological functions. The most common fluids have been found to contain as major components reduced sulfur compounds such as hydrogen sulfide, dimethyldisulfide, and dimethyltrisulfide as well as other odor sources, for example, isovaleric acid. Other components are amines such as ammonia, triethylamine, indole, and skatole.

Attempts to prevent such odors from forming or to absorb those formed have often involved antimicrobial treatments. The use of additives such as activated carbon, zeolites, metals such as copper, metal oxides, alumina hydrate, minerals such as holmite, laconite, kaolin and modifications of molecular sieves have been suggested as well as the use of acid/base interactions to neutralize the various odor forming components. In spite of these efforts, there remains a need to control such odors without relying on complex structures or modifications of materials to achieve the desired effect.

SUMMARY OF THE INVENTION

The present invention is directed to discovery of the ability of certain compounds, for example, triglycerides and polyglycosides, to enhance malodor absorption properties of compositions and substrates such as naturally occurring polymers like chitosan or alginates and synthetic polymers treated with surfactants. The resulting devices, compositions and materials are much more effective in absorbing odors, particularly those related to biological waste. In applications subject to exposure to bodily exudates such as disposable diapers and training pants, sanitary napkins and tampons, incontinent products and medical dressings, the present invention in the form of treated nonwovens and other structures is particularly effective. Examples include treatment of chitosan with an alkyl polyglycoside and addition of an alkyl polyglycoside to a synthetic polymer melt providing odor absorption plus wettability. In accordance with the invention substrates having an initial absorption for at least one of hydrogen sulfide, dimethyidisulfide, dimethyltrisulfide, isovaleric acid, ammonia, triethylamine, indole and skatole of at least about 1%, particularly at least about 34%, more particularly at least about 44% is provided with an increase in its ability to absorb at least one of the odors by at least about 50%, particularly at least about 100% and more particularly at least about 500%.

DETAILED DESCRIPTION OF EMBODIMENTS

Definitions

As used herein the term "nonwoven fabric or web" means a web having a structure of individual fibers or threads which are interlaid, but not in a regular or identifiable manner as in a knitted or woven fabric. Nonwoven fabrics or webs have been formed from many processes such as for example, meltblowing processes, spunbonding processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91). As used herein the term "microfibers" means small diameter fibers having an average diameter not greater than about 75 microns, for example, having an average diameter of from about 0.5 microns to about 50 microns, or more particularly, microfibers may have an average diameter of from about 2 microns to about 40 microns. Another frequently used expression of fiber diameter is denier, which is defined as grams per 9000 meters of a fiber and may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by .00707. Thus, a 15 micron polypropylene fiber has a denier of about 1.42 ($15^2$ ×0.89×0.00707=1.415). Outside the United States the unit of measurement is more commonly the "tex", which is defined as the grams per kilometer of fiber. Tex may be calculated as denier/9.

As used herein the term "spunbonded fibers" refers to small diameter fibers which are formed by extruding molten thermoplastic material as filaments from a plurality of fine, usually circular, capillaries of a spinneret with the diameter of the extruded filaments then being rapidly reduced as by methods described, for example, in U.S. Pat. Nos. 4,340,563 to Appel et al., 3,692,618 to Dorschner et al., 3,802,817 to Matsuki et al., 3,338,992 and 3,341,394 to Kinney, 3,502,763 to Hartmann, 3,502,538 to Levy, and 3,542,615 to Dobo et al., each of which is incorporated herein in its entirety by reference. Spunbond fibers are generally not tacky when they are deposited onto a collecting surface and undergo a separate bonding step for integrity such as thermal point bonding defined below. Spunbond fibers are quenched and generally continuous and usually have average diameters larger than about 7 microns, more particularly, between about 10 and 20 microns.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" includes all possible geometrical configurations of the material. These configurations include, but are not limited to isotactic, syndiotactic and random symmetries.

As used herein the term "monocomponent" fiber refers to a fiber formed from one or more extruders using only one polymer. This is not meant to exclude fibers formed from one polymer to which small amounts of additives have been added for color, anti-static properties, lubrication, hydrophilicity, etc. These additives, e.g. titanium dioxide for color, are generally present in an amount less than 5 weight percent and more typically about 2 weight percent.

As used herein the term "conjugate fibers" refers to fibers which have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement or an "islands-in-the-sea" arrangement. Conjugate fibers are taught in U.S. Pat. Nos. 5,108,820 to Kaneko et al., 5,336,552 to Strack et al., and 5,382,400 to Pike et al., each of which is incorporated herein in its entirety by reference. For two component fibers, the polymers may be present in ratios of 75/25, 50/50, 25/75 or any other desired ratios.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein the term "blend" as applied to polymers, means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein "thermal point bonding" involves passing a fabric or web of fibers to be bonded between a heated calender roll and an anvil roll. The calender roll is usually, though not always, patterned in some way so that the entire fabric is not bonded across its entire surface. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings which is incorporated herein in its entirety by reference. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5%. Another typical point bonding pattern is the expanded Hansen and Pennings or "EHP" bond pattern which produces a 15% bond area with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15%. Yet another common pattern is the C-Star pattern which has a bond area of about 16.9%. The C-Star pattern has a cross-directional bar or "corduroy" design interrupted by shooting stars. Other common patterns include a diamond pattern with repeating and slightly offset diamonds and a wire weave pattern looking as the name suggests, e.g. like a window screen. Typically, the percent bonding area varies from around 10% to around 30% of the area of the fabric laminate web. As is well known in the art, the spot bonding holds the laminate layers together as well as imparts integrity to each individual layer by bonding filaments and/or fibers within each layer.

As used herein, the term "personal care product" means diapers, training pants, absorbent underpants, adult incontinence products, and feminine hygiene products.

As used herein the term "indole" refers to a common fecal odor that is usually associated with the breakdown of tryptophan derived from amino acids. It is a pyrrole (2,3 benzopyrrole) with a molecular formula of $C_8H_7N$, a molecular weight of 117.14 g., and a melting point of 52° C. It is soluble in hot water, hot alcohol, ether and benzene.

As used herein the term "skatole" refers to another common fecal odor, and it has origins similar to that of indole. Skatole is actually a methylated version of indole, and it is also referred to as "3-methylindole". The molecular formula is $C_9H_9N_9$ with a molecular weight of 131.17 g., and it has a melting point of 95° C. It is soluble in hot water, alcohol, benzene, chloroform, and ether.

As used herein "isovaleric acid", (IVA) also called "3-methylbutanoic acid" is a compound with a rancid cheese odor that is commonly associated with vomit. It has a molecular formula of $C_5H_{10}O_2$, and it has a molecular weight of 102.13 g. It is soluble in low concentrations in water, and soluble in alcohol, chloroform and ether.

As used herein both "dimethyldisulfide" (DMDS) and "dimethyltrisulfide" (DMTS) refer to reduced sulfur compounds that are associated with the amino acid metabolism.

Dimethyidisulfide has a molecular formula and weight of $C_3H_6S_2$ and 94.20 g. respectively. Dimethyltrisulfide, on the other hand, is more difficult to describe. It is believed to have a formula of $C_3H_6S_3$ and a molecular weight of 126.2 g.

As used herein "triethylamine" (TEA) refers to a compound that is usually a consequence of alkylation of ammonia in the vapor phase. It smells strongly of ammonia and is alternatively referred to as N,N-Diethylethananamine with a molecular formula of $C_6H_5N$ and a molecular weight of 101.19 g. It is slightly soluble in water at 25° C. and is miscible with alcohol, ether, and water below 18.7° C. "Ammonia" has a molecular formula of $H_3N$ and is usually associated with bacterial decomposition of urea to ammonia:

Urea (in urine)+Urease (in bacteria) >>>>>Ammonia

It is soluble in water, ethanol, methanol, chloroform and ether. The human nose can sense very low concentrations of ammonia.

As used herein a given range is intended to include any and all lesser included ranges.

For example, a range of from 50–100 would also include 60–90, 55 to 80, and the like.

As used herein the term "consisting essentially of" does not exclude the presence of additional materials which do not significantly affect the desired characteristics of a given composition. Examples include, without limitation, pigments, fillers, flow promoters, and the like. As used herein and in the claims, the term "comprising" is inclusive or open-ended and does not exclude additional unrecited elements, compositional components, or method steps.

Test Procedures

Analysis of the odor reducing capabilities of each of the polymeric examples was performed using standard Headspace Gas Chromatography techniques as follows.

A flame ionization detector (FID) was used to analyze all the malodors except ammonia. An FID responds to compounds that produce ions when burned in a hydrogen-air flame. Ammonia is an inorganic compound and does not readily produce ions when burned. Therefore a thermal conductivity detector (TCD) was needed to do the analysis with ammonia. A TCD, has two channels (one a reference (carrier gas) and the other has the effluent from the analytical column) to transfer heat to a thermister. The different thermal conductivities cause a difference in temperature which is proportional to the amount of analyte.

Two different GC columns were used. The column used in conjunction with the FID is described below:

DB-210 capillary column 30 m in length 0.25 mm internal diameter 0.5 micron film thickness The column used for ammonia and the TCD is described below:

DB-1 capillary column 60 m in length 0.32 mm internal diameter 0.5 micron film thickness When using the GCHS, pressures and gas flows affect the retention times and peak shapes of the test components. The variables that were held constant for each detector are column head pressure, carrier gas pressure, carrier gas, split vent flow, purge vent flow, detector temperature, and injector temperature. Different column temperature programs were used for each different malodor in order to obtain optimal results. Listed below are the constants and the temperature programs for each malodor.

FID conditions:

Injector Temp: 105° C.

Detector Temp: 300° C.

TCD conditions:

Injector Temp: 105° C.

Detector Temp: 150° C.

Temperature programs used to analyze:

1) TEA, DMDS, and DMTS
   50° C. for 2 minutes, then increase at 20° C./minute up to 160° C.

2) Indole and Skatole
   50° C. for 1 minute, then increase at 20° C./ minute up to 240° C. remain at 240° C. for 2 minutes 3) IVA
   Begin at 50° C. and increase at 20 C./ minute up to 190° C.
   Remain at 190° C. for 1 minute 4) Ammonia
   Begin at 40° C. and increase at 10° C./ minute up to 100° C.

The general procedure used for the analysis involved the steps set out below after the necessary materials were obtained:

20 cc sample vials 2 cc screw cap sample vials with rubber septa vial caps

Teflon coated septum crimper

5 $\mu$L syringe

Step 1—A specific amount of material was weighed in a 20 cc vial.

Step 2—The Teflon septum was placed into the cap with the Teflon facing downward.

Step 3—A specific amount of malodor was drawn from the 2 cc vial into the syringe.

Step 4—The malodor was injected into the vial with the tip of the needle touching the side of the vial so that none of the liquid stayed on the tip of the needle.

Step 5—The vial was quickly capped and crimped closed.

Step 6—The vial was placed into headspace sampler to incubate at 37° C. for at least 15 minutes.

Step 7—The GC test was run on the sequence of vials.

Malodor Preparation

For each vial tested a very specific amount of the malodors was injected. Care was taken to exactly repeat the procedure of injecting. To save time some of the malodors were grouped together into one stock solution. Stock solutions of each chemical were kept in 2 cc screw cap vials that had a rubber septum.

The stock solutions of DMDS, DMTS, and TEA were taken directly from the bottles containing the chemicals. All three were in the liquid state to begin with, therefore it was not necessary to make any alterations before injecting. The DMDS was 98% pure and 0.5 $\mu$L of this undiluted liquid was used for each test. The DMTS was 98+% pure and 0.5 $\mu$L of this undiluted liquid was also used for each test. The TEA used was 99+% pure and again 0.5 $\mu$L of the undiluted liquid was used. Each chemical (DMDS, DMTS, and TEA) was separately introduced in the same vial. Each chemical was injected into the test vials in an amount of 0.5 $\mu$L.

Because indole and skatole were also tested simultaneously, together the stock solution of indole and skatole was made up to be 20% indole and 20% skatole in methylene chloride. Both compounds are solid in their natural states. The indole used was 99+% pure and the skatole used was 98% pure. This stock solution was injected in an amount of 1 $\mu$L into each vial for testing. In this case the vial was not immediately capped and crimped. The vial was allowed to air out for 1.5–2 minutes to let some of the solvent MeCl$_2$ evaporate out since during GC analysis a solvent can compete with the actual components of interest.

IVA was tested alone. The stock solution was taken directly from the bottle containing the chemical. It is in the liquid state to begin with, and, therefore, it was not necessary to make any alterations before injecting. This undiluted 99% pure chemical was injected in an amount of 0.5 µL into each testing vial.

Ammonia was also tested alone, but it was actually ammonium hydroxide that was injected into the sample vials. The ammonium hydroxide is in the liquid form and was 30% pure. It undergoes a reaction which produces ammonia and water. To ensure that ammonia was present in the test vial, a sample was tested in a mass spectrometer. The amount used for testing was 2µL of the ammonium hydroxide solution.

The control data were obtained by running vials in the GC with only the specific amount of the stock solutions present. Those data were compared later to the vials with an absorbent present to find the percent difference.

EXAMPLES

The invention will be illustrated by several examples. As will be understood by those skilled in this art, the invention is not limited to the presented examples and is broadly applicable within the scope of the appended claims.

The examples demonstrate classes of polymers and absorbents including both synthetic polymers, e.g. polyolefins, and natural polymers, e.g. chitosan, chitin, cellulose, and alginates. Classes of surfactants include alkyl polyglycosides and mixtures of castor oil derivatives (e.g. ethoxylated castor oil) and sorbitan alkyl esters (e.g. sorbitan monooleate). As the examples demonstrate, the odors are absorbed without a surfactant, and these results are improved with the addition of a surfactant. In the case of chitosan, for example, the ability to absorb isovaleric acid, dimethyidisulfide and dimethyltrisulfide is increased dramatically above the untreated control.

Comparative Example 1

This will serve as a basis for all other examples that follow.

In this example activated carbon commercially referred to as Sorb-A-Odor was weighed and presented in a 20 ml test vial for GC analysis. After weighing the activated carbon, a known concentration of volatile was also introduced and the vial was closed immediately upon introduction of the volatile. The vials were introduced in the headspace and maintained at 37 degrees C. After incubating for about 15 minutes, the space above the sample was injected into the GC to analyze for the remaining volatile.

Samples of activated carbon weighed an average of 10.5 mg and were subjected to exposure to various volatile compounds. The amount of volatile absorbed on a % basis relative to their initial concentration was determined in each case. The initial amounts of the volatiles added to the 20 ml vials were as follows: 0.4685 mg isovaleric acid, 0.52 mg dimethyl disulfide, 0.5 mg dimethyl trisulfide, 0.7 mg triethylamine,1 mg indole, and 1 mg skatole. The results of the absorption of the volatiles on a minimum of triplicate samples, given in % absorbed was as follows: 99.8% for isovaleric acid, 99.4% for dimethyl disulfide, 100% for dimethyl trisulfide, 100% for triethylamine, 71% indole and 18.5% skatole.

Comparative Example 2

Under conditions specified in COMPARATIVE EXAMPLE 1, Absents®, a commercially available molecular sieve obtained from UOP Industries and distributed by Gordon Laboratories, Upper Darby, Pa. was subjected to all of the volatiles listed above and was introduced at various weights with the following results: 15 mg absorbed 99.8% isovaleric acid; 40 mg absorbed 99.7 % dimethyldisulfide and 99.9 % dimetyltrisulfide, and 100% triethylamine; and 15 mg absorbed 68% indole and 32% skatole.

comparative Example 3

Also under conditions described in COMPARATIVE EXAMPLE 1, Arm and Hammer® Baking Soda (purchased off the shelf) introduced at 50 mg absorbed 98.2% isovaleric acid; and 150 mg absorbed 8% dimethyidisulfide, 10% dimethyltrisulfide, 0% triethylamine,1 % indole, and 1 % skatole.

Comparative Example 4

Chitin (VNS-647) obtained directly from Vanson Industries, Redmond, WA provided as a flaky material was subjected to the same volatiles with the following results: 10 mg absorbed 92.5% isovaleric acid, 0% dimethyidisulfide, 45% dimethyltrisulfide, 24% triethylamine, 77% indole and 60% skatole.

Comparative Example 5

Chitosan, the deacetylated form of chitin was studied as a natural material to help abate odors. Chitosan (version RNS-022 from Vanson) films were prepared by dissolving the polymer in 2% acetic acid and casting a film using a doctor's blade. Ten mg of chitosan acetate was able to absorb an average of 60% isovaleric acid, 1% dimethyidisulfide, 8% dimethyltrisulfide, 44% triethylamine, 90% indole and 67% skatole.

Example 5A

Chitosan treated with 0.5% Glucopon 220UP alkyl polyglycoside from Henkel Corporation by weight was also fashioned into a film similar to the method described in COMPARATIVE EXAMPLE 5. Ten mg of that film was able to absorb an average of 97% of isovaleric acid, 18% dimethyldisulfide, 36% dimethyltrisulfide, 34% triethylamine, 84% indole and 58% skatole.

Comparing EXAMPLE 5A to COMPARATIVE EXAMPLE 5 demonstrates the ability of an alkyl polyglycoside to increase the ability of chitosan to absorb isovaleric acid by 61%, dimethyldisulfide by 1800%, and dimethyltrisulfide by 450%

Example 6

Chitosan treated by adding 1% Glucopon by weight was also fashioned into a film similar to the method described in COMPARATIVE EXAMPLE 5. Ten mg of that film was able to absorb an average of 99% of isovaleric acid, 6% dimethyldisulfide, 46% dimethyltrisulfide, 54% triethylamine, 92% indole and 74% skatole.

Comparing EXAMPLE 6 to COMPARATIVE EXAMPLE 5 demonstrates the ability of an alkyl polyglycoside to increase the ability of chitosan to increase the ability of the polymer to absorb isovaleric acid by 65%, dimethyidisulfide by 600%, and dimethyltrisulfide by 575%.

Comparative Example 7

Calcium alginate fiber tows with and without additives were prepared by wet spinning sodium alginate in a C$_4$Cl$_2$ solution, heat treating the resulting fibers. These were also subjected to odor absorption studies. Samples of the tows were cut into 10 mg sample quantities and subjected to the same volatiles described in COMPARATIVE EXAMPLE 1. The samples of calcium alginate fiber tows that were tested are designated at Samples A, B, C, and D below:

Sample A: calcium alginate (no additives), control
Sample B: calcium alginate with 8% Absents® (the Absents described in COMPARATIVE EXAMPLE 2)
Sample C: calcium alginate with 4% activated carbon (the same activated carbon as in COMPARATIVE EXAMPLE 1)
Sample D: calcium alginate with 2% chitosan (the same chitosan used in COMPARATIVE EXAMPLE 5)

The following Table shows the absorption characteristics of the calcium alginate fibers.

TABLE

| | % Volatile Absorbed | | | | | | |
|---|---|---|---|---|---|---|---|
| Sample | IVA | TEA | DMDS | DMTS | Indole | Skatole | Ammonia |
| A | 95 | 65 | 13 | 26 | 82 | 25 | 100 |
| B | 97 | 83 | 7 | 45 | 84 | 46 | 96 |
| C | 98 | 38 | 0 | 0 | 87 | 40 | 94 |
| D | 99 | 80 | 28 | 44 | 86 | 43 | 98 | where
IVA = isovaleric acid
TEA = triethylamine
DMDS = dimethyldisulfide
DMTS = dimethyltrisulfide where
IVA=isovaleric acid
TEA=triethylamine
DMDS=dimethyldisulfide
DMTS=dimethyltrisulfide It is believed that the above calcium alginate embodiments will also benefit from combination with alkyl polyglycosides. As has been shown, the effective amount of alkyl polyglycoside varies widely depending on the other odor absorbing components as well as the nature of the odor being absorbed. Useful amounts will often be in the range of from trace to 50% based on the total weight of odor absorbing components with higher amounts than 50% also useful but less cost effective. In many cases an amount up to about 10% will be more cost effective. As shown by COMPARATIVE EXAMPLE 7, the other odor absorbing component may comprise essentially 100% of the structure in which case lower percent values of the alkyl polyglycoside may be used. Other substrates such as monocomponent, multicomponent and multiconstituent nonwovens may be treated as well with varying degrees of success depending on polymers, treatments and odors being absorbed.

As has been demonstrated, the invention significantly improves odor reduction by absorption of malodors. It will be apparent that the invention is applicable to many variations and alternatives and is useful in a wide variety of products, including those for containment of bodily exudates, for example. Other alternatives, modifications and variations will be apparent to those skilled in the art in light of the foregoing description. It is intended to embrace within the appended claims all such alternatives, modifications and variations and equivalents thereof. In this regard it is intended that such equivalents include functional as well as structural and compositional equivalents. For example, a screw and a nail are functional equivalents for attaching materials even though they may not have the same structure.

We claim:

1. A personal care device adapted to receive bodily exudates and control malodors associated therewith comprising, a substrate having malodor absorption properties and comprising a film or web containing a chitosan or alginate or a surfactant treated synthetic fiber web; and contained on or in said substrate, an amount of a triglyceride and/or a polyglycoside composition effective to increase the malodor absorption properties of said personal care device by at least about 50% when compared with said personal care device without said triglyceride and/or polyglycoside using a malodor selected from the group consisting of indole, skatole, isovaleric acid, dimethyldisulfide, dimethyltrisulfide, triethylamine and ammonia.

2. The device of claim 1 wherein said substrate is selected from the group consisting of chitosans and alginates and said composition comprises an alkyl polyglycoside.

3. The device of claim 2 wherein said substrate comprises a chitosan.

4. The device of claim 2 wherein said substrate comprises an alginate.

5. The device of claim 1 wherein said substrate is in the form of a surfactant treated synthetic fiber web.

6. The device of claim 1 wherein said improvement is in the range of at least about 100%.

7. The device of claim 6 wherein said improvement is in the range of at least about 500%.

8. The device of claim 1 wherein said substrate is selected from the group consisting of chitosans and alginates, and said composition comprises a triglyceride.

9. The device of claim 8 wherein said substrate comprises a chitosan.

10. The device of claim 8 wherein said substrate comprises an alginate.

11. The device of claim 2 wherein said substrate is in the form of a surfactant treated synthetic fiber web.

12. The device of claim 6 wherein said substrate is in the form of a surfactant treated synthetic fiber web.

13. The device of claim 8 wherein said improvement is in the range of at least about 100%.

14. The device of claim 13 wherein said improvement is in the range of at least about 500%.

15. The device of claim 1 wherein said malodor is selected from the group consisting of dimethytrisulfide and dimethyldisulfide and said improvement exceeds 100%.

* * * * *